United States Patent [19]

Bosies et al.

[11] 4,409,236
[45] Oct. 11, 1983

[54] N-SUBSTITUTED AZIRIDINE-2-CARBOXYLIC ACID DERIVATIVES AND IMMUNO-STIMULATION COMPOSITION AND METHOD

[75] Inventors: Elmar Bosies, Weinheim; Herbert Berger, Mannheim; Wolfgang Kampe, Heddesheim; Uwe Bicker, Mannheim; Alfred Grafe, Mörlenbach, all of Fed. Rep. of Germany

[73] Assignee: Boehringer Mannheim GmbH, Mannheim, Fed. Rep. of Germany

[21] Appl. No.: 268,964

[22] Filed: Jun. 1, 1981

Related U.S. Application Data

[62] Division of Ser. No. 59,863, Jul. 23, 1979, Pat. No. 4,321,194.

[30] Foreign Application Priority Data

Aug. 3, 1978 [DE] Fed. Rep. of Germany ....... 2833986

[51] Int. Cl.³ ................ A61K 31/395; C07D 203/08; C07D 333/30
[52] U.S. Cl. ...................................... 424/275; 549/59
[58] Field of Search ........................... 549/59; 424/275

[56] References Cited

PUBLICATIONS

Gundermann et al., Berichte 105, 312–324, (1972).

Primary Examiner—John M. Ford
Assistant Examiner—Bernard Dentz
Attorney, Agent, or Firm—Sprung, Horn, Kramer & Woods

[57] ABSTRACT

Aziridine-2-carboxylic acid derivatives of the formula

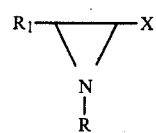

wherein
X is a carboxyl, nitrile, alkoxycarbonyl or carbamoyl group, and
R and $R^1$ are various organic radicals; or pharmacologically acceptable salts thereof, exhibit marked immunostimulant activity, especially in conjunction with added chemotherapeutic agents such as a penicillin, a cephalosporin, a nitrofuran or chloramphenicol. Those compounds are new where X is a cyano group or an alkoxycarbonyl radical and $R_1$ is a hydrogen atom, but R' is not an unsubstituted alkyl radical or an alkyl radical substituted by hydroxyl, alkoxy, dialkylamino, phenyl, 4-chlorophenyl or 4-methoxyphenyl or a vinyl radical substituted by a phenyl or methyl radical, or a cycloalkyl radical, a phenyl, a 4-chlorophenyl, a 4-methoxyphenyl, an s-triazinyl or a pyridinyl radical; or where X is a carbamoyl group and $R_1$ is a hydrogen atom, R' is not an unsubstituted cyclohexyl, alkyl or benzyl radical; or where X is a cyano group or an alkoxycarbonyl radical and $R_1$ is a phenyl radical, R' is not an isopropyl, cyclohexyl, phenyl, benzyl or p-chlorobenzyl radical; or where $R_1$ is a methyl radical, $R^1$ is not a benzyl, p-chloro- or p- methoxybenzyl radical.

4 Claims, No Drawings

N-SUBSTITUTED AZIRIDINE-2-CARBOXYLIC ACID DERIVATIVES AND IMMUNO-STIMULATION COMPOSITION AND METHOD

This is a division of application Ser. No. 059,863, filed July 23, 1979 now U.S. Pat. No. 4,321,194.

The present invention is concerned with pharmaceutical compositions containing N-substituted aziridine-2-carboxylic acid derivatives, some of which are new, and with the preparation of such N-substituted aziridine-2-carboxylic acid derivatives.

It is known that aziridines, because of their structure and properties, belong to the alkylating-acting compounds, for example cyclophosphamide compounds, which play an important part in the therapy of cancer. Unfortunately, the alkylating action does not take place selectively with the components of the cancer cells so that these compounds can also act cancerogenically on normal cells. However, substitution with a cyano group in the 2-position of the aziridine rings showed that the ability to alkylate and thus also the toxicity was lost.

German Democratic Republic Patent Specification No. 110,492 describes 1-carbamoyl-2-cyanoaziridine which, when administered intravenously to rats, bring about a very marked increase of the leukocytes and lymphocytes, whereas the number of erythrocytes remains almost unchanged. Furthermore, a considerable multiplication of the antibody-forming spleen cells was observed. Therefore, this compound can be used as an immune-stimulating therapeutic in cases of bacterial and viral infections (see Federal Republic of Germany Patent Specification No. 25 28 460.0). However, the low stability of this compound in solution and the complete ineffectiveness when administered orally proved to be serious disadvantages of this compound.

Therefore, the problem exists of finding immune-stimulating therapeutic compounds which, with the same or increased effectiveness and low toxicity, do not display any noteworthy side effects, are more stable and can be more simply administered, preferably orally.

We have now found that this problem is solved by a class of aziridine-2-carboxylic acid derivatives which are substituted on the ring nitrogen atom by alkyl or aryl radicals.

Thus, according to the present invention, there are provided pharmaceutical compositions containing at least one aziridine-2-carboxylic acid derivative which is substituted on the ring nitrogen atom and which have the general formula:

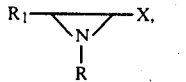  (I)

wherein X is a carboxyl or nitrile group or an alkoxycarbonyl radical or an unsubstituted or substituted carbamoyl group; R is a straight-chained or branched, saturated or mono- or poly-unsaturated aliphatic hydrocarbon radical which is optionally substituted one or more times by halogen, alkoxy, hydroxyl, dialkylamino, cycloalkylamino, acylamino, acyl, nitro, alkylthio, alkylsulphinyl, alkylsulphonyl, nitrile, carbalkoxy or carbamoyl radicals or by cycloalkyl radicals optionally substituted by alkyl, alkoxy or carbalkoxy, or by cycloalkenyl radicals, which can optionally be bridged, or by an aliphatic or aromatic heterocyclic radical, by aryl, aryloxy, arylthio, acyloxy, alkoxycarbonylamino or ureido groups, or R is a cycloalkyl or cycloalkenyl radical containing 3 to 10 carbon atoms which is optionally substituted by alkyl, alkoxy, alkoxycarbonyl or oxo groups and is also optionally interrupted by hetero atoms and optionally bridged by 1 to 3 carbon atoms, or R is an aryl or hetaryl radical, the aryl and hetaryl radicals being optionally substituted by halogen, alkoxy, alkyl, hydroxyl, carbalkoxy, carbamoyl, dialkylamino, cycloalkylamino, acylamino, nitro, cyano, acyl, alkylthio, alkylsulphinyl, alkylsulphonyl, sulphamoyl, phenyl, trifluoromethyl, aryloxy, acyloxy or methylenedioxy; and $R_1$ is a hydrogen atom or a saturated, straight-chained or branched alkyl radical containing up to 4 carbon atoms or a phenyl radical; and/or at least one pharmacologically-acceptable salt thereof, in admixture with a solid or liquid pharmaceutical diluent or carrier.

The immune stimulation of these compounds of general formula (I) was demonstrated by:

1. an increase of the leukocytes and lymphocytes after oral and intravenous administration thereof;
2. an increase of the lymphocyte transformation, measured with the use of the incorporation of radioactively-marked thymidine into human lymphocytes after incubation with the above-mentioned compounds (see K.Resch in "Praxis der Immunologie", ed. K. O. Vorlaender, pub. Thieme-Verlag, Stuttgart, 1976);
3. the use of animal experimental infection in mice in which it was possible to show that the additional administration of the above-mentioned compounds to known bacteriostatically-acting chemotherapeutic compounds, for example chloramphenicol, produced a clearly improved therapeutic effect in comparison with the sole administration of the bacteriostatic chemotherapeutic, for example, chloramphenicol.

Consequently, the present invention also provides pharmaceutical compositions which, in addition to containing at least one compound of general formula (I) and an appropriate carrier, also contain at least one known chemotherapeutic agent.

A chemotherapeutic agent is generally to be understood to be a substance with an antimicrobial action, for example a penicillin or cephalosporin compound, as well as a compound of the nitrofuran group.

The synergistic effect is shown, for example, in the case of a pharmaceutical combination which contains an immune stimulant compound of general formula (I) and the bacteriostatically-acting chemotherapeutic compound chloramphenicol.

The present invention includes within its scope all stereoisomeric compounds of general formula (I) which, for example, exist because of asymmetric carbon atoms or of cis-trans isomerism, the separation of which into the stereoisomeric forms can be carried out by known processes.

The term "alkyl", if not stated otherwise, is to be understood to mean, alone or in combination, for example in alkoxy, alkoxycarbonyl, N-alkylamino, alkylthio, alkylsulphinyl and alkylsulphonyl radicals, a straight-chained or branched chain containing up to 8 carbon atoms. Preferred alkyl radicals include methyl ethyl, n-propyl, isopropyl, n-butyl, sec.-butyl, tert.-butyl, n-pentyl, neo-pentyl and n-hexyl radicals. The alkyl chain can optionally be substituted by, for example, halogen, such as chlorine, or by hydroxyl, nitro or cyano. Further substituents which can be present include amino groups, preferably dimethylamino and 2-cyanoaziridin-1-yl radicals, acylamino radicals, for example, formamido, acetamido and benzamido radicals, and carbamoyl, carbalkoxy and alkoxy radicals.

The mono- and poly-unsaturated aliphatic hydrocarbon radicals are to be understood to be radicals which contain 3 to 8 and preferably 3 to 5 carbon atoms, with at least one double and/or triple bond in any desired position of the unsaturated chain, preferred radicals of this type including the vinyl, allyl, methallyl, crotyl, 2-methylpropenyl, propargyl, but-2-ynyl, but-3-ynyl and pent-3-enyl radicals.

The cycloalkyl and cycloalkenyl radicals are to be understood to be those containing 3 to 10 carbon atoms, especially the cyclopropyl, cyclopentyl, cyclohexyl, cyclohexenyl, cycloheptenyl and 3,6-dioxo-1,4-cyclohexadienyl radicals, as well as cycloalkyl radicals bridged with 1 to 3 carbon atoms, for example the norbornyl and adamantyl radicals. The cycloalkyl and cycloalkenyl radicals interrupted by hetero atoms are preferably the tetrahydrofuryl, tetrahydropyranyl, thienyl, optionally substituted piperidinyl, morpholinyl and pyrrolidinyl radicals, as well as the N-methyl-3,4-dehydropiperidinyl and the N-methyl-piperazinyl radicals.

The aryl radicals, alone or in combination, for example in aryloxy and arylthio radicals, the aromatic carbocyclic radicals and preferably phenyl, naphthyl, anthracenyl, phenanthrenyl and fluorenyl radicals.

By hetaryl radicals, there are to be understood aromatic ring systems containing 5 or 6 members and one or more hetero atoms, for example, oxygen, sulphur or alkylated or acylated nitrogen, which can also be condensed with one or two benzene rings or with another heterocycle. Preferred radicals of this type include the pyridyl, quinolyl, furyl, thienyl, benzofuryl, imidazolyl, pyrazolyl, thiazolyl, pyrimidinyl, pyridazinyl, s-triazolyl, s-triazinyl and purinyl radicals.

The halogen atoms are to be understood to be fluorine, chlorine and bromine atoms.

By acyl radicals there are to be understood, alone or in combination, for example in acyloxy radicals, the acid residues of organic carboxylic and sulphonic acids, preferred radicals of this type including the formyl, acetyl, benzoyl, furoyl, tosyl and methanesulphonyl radicals.

In all cases, the aryl and hetaryl radicals can be substituted one or more times by the above-mentioned substituents.

When X is a carbamoyl group, it can be optionally substituted by lower alkyl, cycloalkyl, aryl and acyl radicals.

Some of the compounds of general formula (I), in which $R_1$ is a hydrogen atom or a methyl or phenyl radical and X is a cyano group or an alkoxycarbonyl radical, are known from the literature. Thus, for example, the lower N-alkyl-2-cyanoaziridines, the alkyl radical of which is unsubstituted, 1-benzyl-2-cyanoaziridine and the like, have been described by Gundermann et al. (Chem. Ber., 105, 312–315). Other compounds have been described in Federal Republic of Germany Patent Specification No. 25 30 960. All the known compounds have been described as intermediates without any mention of a pharmacological effectiveness so that it was surprising that these compounds also have an immune-stimulating action.

The present invention also provides new compounds of the general formula:

wherein X is a carboxy or nitrile group or an alkoxycarbonyl radical or an unsubstituted or substituted carbamoyl group, R' is a straight-chained or branched, saturated or mono- or polyunsaturated aliphatic hydrocarbon radical which is optionally substituted one or more times by halogen, alkoxy, hydroxyl, dialkylamino, cycloalkylamino, acylamino, acyl, nitro, alkylthio, alkylsulphinyl, alkylsulphonyl, nitrile, carbalkoxy or carbamoyl radicals or by cycloalkyl radicals optionally substituted by alkyl, alkoxy or carbalkoxy, or by cycloalkenyl radicals, which can optionally be bridged, or by an aliphatic or aromatic heterocyclic radical, by aryl, aryloxy, arylthio, acyloxy, alkoxycarbonylamino or ureido groups, or R' is a cycloalkyl or cycloalkenyl radical containing 3 to 10 carbon atoms which is optionally substituted by alkyl, alkoxy, alkoxycarbonyl or oxo groups and is also optionally interrupted by hetero atoms and optionally bridged by 1 to 3 carbon atoms, or R' is an aryl or hetaryl radical, the aryl and hetaryl radicals being optionally substituted by halogen, alkoxy, alkyl, hydroxyl, carbalkoxy, carbamoyl, dialkylamino, cycloalkylamino, acylamino, nitro, cyano, acyl, alkylthio, alkylsulphinyl, alkylsulphonyl, sulphamoyl, phenyl, trifluoromethyl, aryloxy, acyloxy or methylenedioxy; and $R_1$ is a hydrogen atom or a saturated, straight-chained or branched alkyl radical containing up to 4 carbon atoms or phenyl radical, with the proviso that when X is a cyano group or an alkoxycarbonyl radical and $R_1$ is a hydrogen atom, R' is not an unsubstituted alkyl radical or an alkyl radical substituted by hydroxyl, alkoxy, dialkylamino, phenyl, 4-chlorophenyl or 4-methoxyphenyl or a vinyl radical substituted by a phenyl or methyl radical, or a cycloalkyl radical, a phenyl, a 4-chlorophenyl, a 4-methoxyphenyl, an s-triazinyl or a pyridinyl radical and with the proviso that when X is a carbamoyl group and $R_1$ is a hydrogen atom, R' is not an unsubstituted cyclohexyl, alkyl or benzyl radical and with the proviso that when X is a cyano group or an alkoxycarbonyl radical and $R_1$ is a phenyl radical, R' is not an isopropyl, cyclohexyl, phenyl, benzyl or p-chlorobenzyl radical and when $R_1$ is a methyl radical, is not a benzyl, p-chloro- or p-methoxybenzyl radical.

Preferred new compounds of general formula I' according to the present invention include:
2-Cyano-1-(2-methylsulphinylethyl)-aziridine
2-Cyano-1-(2-cyanoethyl)-aziridine
1-(3-Chloropropyl)-2-cyanoaziridine
1-(2-Acetamidoethyl)-2-cyanoaziridine
1-(2-Benzamidoethyl)-2-cyanoaziridine
2-Cyano-1-(2-carbamoylethyl)-aziridine
2-Cyano-1-(but-2-ynyl)-aziridine
2-Cyano-1-(4-hydroxy-3-methoxybenzyl)-aziridine
2-Cyano-1-(cyclohept-2-enylmethyl)-aziridine
2-Cyano-1-(cyclohept-3-enyl)-aziridine
1-(1-Acetylpiperidin-4-yl)-2-cyanoaziridine
2-Cyano-1-(thian-3-yl)-aziridine
2-Cyano-1-(2,2,2-trichloroethyl)-aziridine
2-Cyano-1-(3,4-methylenedioxybenzyl)-aziridine
2-Cyano-1-(2,2,2-trifluoroethyl)-aziridine 2-Cyano-1-(2-nitroethyl)-aziridine
2-Cyano-1-(1-naphthylmethyl)-aziridine
1-Benzyl-aziridine-2-carboxylic acid
1-Allyl-2-cyano-3-phenyl-aziridine
2-Cyano-1-(pent-3-enyl)-aziridine
2-Cyano-1-(4-cyanobenzyl)-aziridine
2-Cyano-1-(2-methylcyclohexyl)-aziridine
2-Cyano-1-(4-methoxycyclohexyl)-aziridine
2-Cyano-1-(pyrimidin-2-yl)-aziridine
2-Cyano-1-(4-phenylbenzyl)-aziridine
2-Cyano-1-(2-methylsulphinylbenzyl)-aziridine
2-Cyano-1-(2-methylsulphonylbenzyl)-aziridine
2-Cyano-1-(4-sulphamoylbenzyl)-aziridine
2-Cyano-1-(3-carbamoylbenzyl)-aziridine
1-(4-Acetylbenzyl)-2-cyanoaziridine
1-(2-Acetamido-5-methylbenzyl)-2-cyanoaziridine
2-Cyano-1-(3,4,5-trimethoxybenzyl)-aziridine
2-Cyano-1-(naphth-1-yl)-aziridine
2-Cyano-1-(thiazol-2-yl)-aziridine
Methyl 2-cyano-1-aziridine-propionate
1-Allyl-2-cyanoaziridine
2-Cyano-1-(3-morpholinopropyl)-aziridine
2-Cyano-1-(2-pyrrolidinoethyl)-aziridine
2-Cyano-1-[3-(2-methylpiperidino)-propyl]-aziridine
2-Cyano-1-(2-α-furoylaminoethyl)-aziridine
2-Cyano-1-(4-methylsulphonamidobenzyl)-aziridine
2-Cyano-1-(4-phenoxybenzyl)-aziridine
Ethyl 3-(2-cyanoaziridin-1-yl)-propionate
2-Cyano-1-(4-hydroxybenzyl)-aziridine
2-Cyano-1-(cyclohex-1 enylmethyl)-aziridine
2-Cyano-1-(2-thenyl)-aziridine
2-Cyano-1-(2-furylmethyl)-aziridine
2-Cyano-1-(2-methylallyl)-aziridine
1-(1-Adamantyl)-2-cyanoaziridine
Ethyl 2-cyano-1-aziridine-acetate
3-(2-Cyano-aziridin-1-yl)-acrolein
Dimethyl 3-(2-cyanoaziridin-1-yl)-fumarate
Ethyl 3-(2-cyanoaziridin-1-yl)-acrylate
1-Phenyl-1-(2-cyanoaziridin-1-yl)-2-cyanoethylene
1-(2-Carbamoylaziridin-1-yl)-1-(p-methoxycarbonylphenyl)ethylene
1-Phenyl-1-(2-carbamoylaziridin-1-yl)-ethylene
1-Phenyl-1-(2-carbamoylaziridin-1-yl)-2-cyanoethylene
1-(2-Carbamoylaziridin-1-yl)-2-carbethoxy-2-cyanoethylene
4-(2-Carbamoylaziridin-1-yl)-1-methyl-3,4-dehydropiperidine
1-Allyl-2-cyano-3-methylaziridine
Ethyl 1-allylaziridine-2-carboxylate
2-Cyano-1-(2-methylthiobenzyl)-aziridine
2-Cyano-1-(3,4-dimethoxybenzyl)-aziridine
2-Cyano-1-(4-methylbenzyl)-aziridine
1-(2-Cyanoaziridin-1-yl)-2-carbethoxy-cyclohex-1-ene; and the pharmacologically-acceptable salts thereof, as well as all the stereoisomeric forms of these compounds.

The compounds of general formula (I') can be prepared in known manner and preferably by one of the following methods:

(a) reaction of a compound of the general formula:

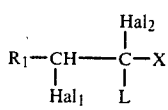

wherein R₁ and X have the same meanings as above, Hal₁ and Hal₂ are chlorine or bromine atoms, L is a hydrogen atom or Hal₁ and L can together represent a valency bond, with an amine of the general formula:

wherein R has the same meaning as above; or (b) reaction of an epoxide of the general formula:

wherein R₁ and X have the same meanings as above, with an amine of general formula (III); or (c) reaction of a compound of the general formula (V) with a compound of the general formula:

wherein T is a hydrogen atom or an alkyl or carboxylic acid ester group and U is an aldehyde or carboxylic acid ester group; or (d) reaction of a compound of the general formula (V) with a compound of the general formula:

wherein B is an optionally substituted alkyl or phenyl radical, D is an optionally substituted alkyl radical or B and D together can represent a ring which is optionally interrupted by hetero atoms; or (e) subjection of an oxazolidinone of the general formula:

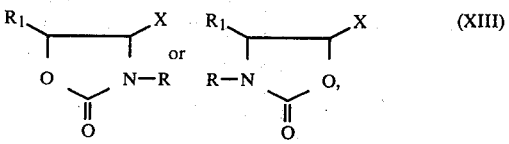

wherein R, R₁ and X have the same meanings as above, to thermolysis; or (f) treatment of a compound of the general formula:

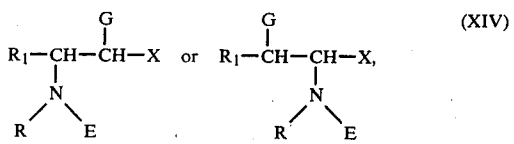

wherein R, R₁ and X have the same meanings as above and G is a hydrogen atom or Hal and E is Hal or a trialkylamino or arylsulphonic acid ester radical, Hal being a chlorine or bromine atom, with a reagent splitting off E-G; whereafter, if desired, a compound obtained of general formula (I) can subsequently be converted into another compound of general formula (I) and, if desired, a compound obtained of general formula (I) can be converted into a pharmacologically-acceptable salt.

Process (a) for the preparation of aziridine derivatives of general formula (I) is known from the literature (see, for example, Gundermann et al., Chem. Ber., 105, 312/1972; and Wagner-Jauregg, Helv. Chim. Acta, 44, 1237/1961). It is preferable to use an inert solvent, for example, diethyl ether, dioxane, benzene, toluene or the like, but it is also possible to use a lower alcohol, for example methanol, ethanol or the like. The reaction temperature can be from 0° to 80° C. and is preferably ambient temperature. The reaction period varies from 3 hours to 10 days.

In the case of process (b), an epoxide of general formula (X) can be reacted with an amine of the general formula (III) and the aminoalcohol thereby obtained dehydrated, to give an aziridine derivative of general formula (I). However, for the conversion of the epoxide into an aziridine, use can also be made of compounds such as $R-N-P(O)(OAlk)_2$- or $Ph_3P=N-R$, wherein R has the same meaning as above. Ph is a phenyl radical and Alk is a lower alkyl radical, for example a methyl or ethyl radical (see Tetrahedron Letters, 1976, 4003 and Chem. Ber. 109, 814/1976).

In the case of processes (c) and (d), the reaction components are, as a rule, reacted without the use of a solvent at a temperature of from 0° to 60° C. The reaction products possibly have to be purified by column chromatography.

Oxazolidinones of general formula (XIII) are, as a rule, thermolyzed without the use of a solvent in the presence of a base, for example, triethanolamine or dicyclohexylethylamine, the reaction product being removed by distillation during the thermolysis. The thermolysis temperature can be from 170° to 250° C.

In the case of process (f), when G is a hydrogen atom, the reagent used for splitting off E-G is preferably an alcoholate, such as an alkali metal methylate or alkali metal ethylate, in the corresponding alcohol. However, it is also possible to use a tertiary amine, for example, triethylamine, triethanolamine or dicyclohexylethylamine, in a solvent, for example, methanol, ethanol, benzene, toluene, diethyl ether or dioxane. When G and E are Hal, the splitting off reaction can be carried out with the use of a conventional dehalogenation agent and preferably with zinc or sodium.

The subsequent conversion of compounds of general formula (I) into other compounds of general formula (I) can be carried out, on the one hand, by conversion of the substituent X. In this case, for example, a compound in which X is an alkoxycarbonyl radical can be converted, by reaction with ammonia, into a compound in which X is a carbamoyl group which, in turn, can be converted with a dehydration agent into a compound in which X is a nitrile group.

Compounds of general formula (I) in which X is an alkoxycarbonyl or carbamoyl group can, therefore, also be used as intermediates for the preparation of compounds of general formula (I) in which X is a nitrile group.

The conversion of an ester group into an amide group can be carried out with gaseous ammonia in an organic solvent, preferably in methanol or ethanol, or with aqueous ammonia at a temperature of from 0° to 25° C. The desired amide either precipitates out or can be isolated from the reaction mixture by, for example, column chromatography.

A carbamoyl group can be converted into a nitrile group by using a dehydration agent known from the literature and preferably with a mixture of triphenylphosphine, carbon tetrachloride and triethylamine. The solvent usually employed is a halogenated hydrocarbon, for example methylene chloride or chloroform, but acetonitrile can also be used. As a rule, the desired nitrile is isolated from the reaction mixture by distillation.

The 2-alkoxycarbonyl-, 2-carbamoyl- and 2-cyanoaziridine derivatives are usually converted into 2-carboxyaziridines by saponification processes which are known from the literature.

For the production of pharmaceutical compositions with immune-stimulating action, the compounds of general formula (I) are mixed in conventional manner with appropriate pharmaceutical carrier materials, optionally granulated and pressed, for example, into tablets or dragee cores. The mixture can also be filled into hard gelatine capsules. With the addition of appropriate adjuvants, there can also be produced a solution or suspension in water, an oil, for example olive oil, or high molecular weight polymer, for example polyethylene glycol, which can then be worked up to give injection solutions, soft gelatine capsules, syrups or drops.

Since the active materials are acid labile, the compositions are either provided with a coating which only dissolves in the alkaline medium of the small intestine or an adjuvant, such as antacid, for example magnesium oxide, which is able to neutralize the gastric juices to a pH value above 6, is incorporated into the formulation.

Examples of solid carrier materials which can be used include starch, starch derivatives, sugar, sugar alcohols, celluloses and cellulose derivatives, tensides, talc, highly-dispersed silicic acids, high molecular weight fatty acids and the salts thereof, gelatine, agar-agar, calcium phosphate, animal and vegetable fats and waxes and solid high molecular weight polymers, for example polyethylene glycols or polyvinylpyrrolidones. If liquid active materials are to be worked up to give tablets or hard gelatine capsules, in addition to highly-dispersed silicic acid, there can also be used carriers, such as phosphates, carbonates and oxides. Compositions suitable for oral administration can, if desired, contain flavoring and/or sweetening agents.

For pharmaceutical combinations in which compounds of general formula (I) are present together with a chemotherapeutic agent, in general there are used the same galenical forms of composition as are described above for the individual substances. The two active materials, i.e. the immune stimulant and the chemotherapeutic agent, are usually present in the composition in a weight ratio of 10:1 to 1:10, it having proved to be advantageous to use an equimolar ratio of the two components.

A preferred composition comprises 100 mg. of chloramphenicol as chemotherapeutic agent and 33.3 mg. of 1-allyl-2-cyanoaziridine, together with appropriate carrier materials, such as starch, and can be produced in the form of a 250 mg. tablet which, as a rule, are taken orally twice a day.

For the demonstration of the immune-stimulating action, there is employed, as already mentioned, on the one hand the influencing of an acute infection with *Escherichia coli* (108) in mice by an immune stimulant selected from compounds of general formula (I), for example 1-allyl-2-cyanoaziridine (B), with the simultaneous administration of a subtherapeutic dose of chloramphenicol (A).

Experimental Protocoll

Groups of 20 female adult NMRI mice (body weight 25 to 30 g.) were, on 0 day, infected with $1.0 \times 10^7$ micro-organisms/animal (*Escherichia coli*) intraperitoneally. Treatment was carried out as follows:

1st Group: 40 mg./kg. A, oral, dissolved in 0.5% tylose solution

2nd Group: 13.4 mg./kg. B, oral, dissolved in 0.5% tylose solution

3rd Group: 40 mg./kg. A+13.4 mg./kg. B, oral, dissolved in 0.5% tylose solution

4th Group: 10 mg./kg. A, oral, dissolved in 0.5% tylose solution

5th Group: 3.3 mg./kg. B, oral, dissolved in 0.5% tylose solution

6th Group: 10 mg./kg. A+3.3 mg./kg. B, oral, dissolved in 0.5% tylose solution

7th Group: control: tylose solution.

Results.

| GROUP | A mg/kg. | | B mg/kg. | % Survival | | | | | |
|---|---|---|---|---|---|---|---|---|---|
| | | | | 1st day | 2nd day | 3rd day | 4th day | 5th day | 6th day |
| 1 | 40 | | — | 70 | 70 | 65 | 65 | 65 | 65 |
| 2 | — | | 13.4 | 0 | 0 | 0 | 0 | 0 | 0 |
| 3 | 40 | + | 13.4 | 100 | 100 | 100 | 100 | 100 | 100 |
| 4 | 10 | | — | 15 | 15 | 15 | 15 | 15 | 15 |
| 5 | — | | 3.3 | 10 | 10 | 10 | 10 | 10 | 10 |
| 6 | 10 | + | 3.3 | 65 | 55 | 50 | 50 | 50 | 50 |
| Control | 0 | | 0 | 0 | 0 | 0 | 0 | 0 | 0 |

On the other hand, in a leukocyte screening test, the increase of the leukocytes after oral administration of compounds of general formula (I) was determined.

Experimental Protocoll

Groups of 10 female, adult Sprague-Dawley rats were fasted and then blood was sampled from the retro-orbital=venous complex and the leukocytes counted with the help of a Coulter counter. Subsequently, the compounds to be investigated were administered orally in a dosage of 200 mg./kg., dissolved or suspended in 0.5% tylose solution. 4 days later, again after fasting overnight, blood was taken from the retro-orbital venous complex and the leukocytes counted in a Coulter counter and the average values, with standard deviations from the average value, were calculated.

| Substance | Results: | | Example |
|---|---|---|---|
| | 0 day | 4th day | |
| B | 8.5 | 17.1 | 1 |
| C | 8.93 | 12.84 | 1 (a) |
| D | 8.0 | 13.5 | 1 (b) |
| E | 8.0 | 14.3 | 1 (f) |
| F | 6.7 | 16.2 | 5 |
| G | 7.55 | 10.4 | 5 (b) |
| H | 7.37 | 8.5 | 7 (b) |
| I | 6.5 | 11.2 | 1 (c) |
| J | 6.5 | 9.6 | 1 (n) |
| K | 8.9 | 12.0 | 1 (p) |
| L | 7.1 | 11.3 | 11 (f) |
| M | 7.1 | 12.3 | 13 (o) |
| N | 7.4 | 11.3 | 16 (a) |
| O | 7.0 | 13.7 | 13 (a) |
| P | 6.6 | 10.6 | 13 (c) |
| Q | 6.3 | 11.9 | 13 (d) |
| R | 7.9 | 12.3 | 13 (x) |
| S | 7.5 | 13.5 | 13 (v) |
| T | 7.0 | 13.2 | 13 (c) |
| U | 8.0 | 11.9 | 6 (b) |
| V | 7.8 | 11.9 | 6 (c) |
| W | 6.9 | 10.6 | 6 (d) |
| X | 5.8 | 11.9 | 13 (w) |
| Z | 6.7 | 9.8 | 13 (i) |

A = Chloramphenicol
B = 1-Allyl-2-cyanoaziridine
C = 2-Cyano-1-methylaziridine
D = 2-Cyano-1-n-propylaziridine
E = 1-Benzyl-2-cyanoaziridine
F = 3-(2-Cyanoaziridin-1-yl)-acrolein
G = Ethyl 3-(2-Cyanoaziridin-1-yl)-acrylate
H = 1-Phenyl-1-(2-carbamoylaziridin-1-yl)-2-cyanoethylene.
I = 2-Cyano-1-isopropylaziridine
J = 2-Cyano-1-(2-thenyl)-aziridine
K = 2-Cyano-1-(2-methylallyl)-aziridine
L = 1-(2-Chloroethyl)-2-cyanoaziridine
M = 2-Cyano-1-(3-trifluoromethylbenzyl)-aziridine
N = 2-Cyano-1-(5-carboxy-2-furfuryl)-aziridine
O = 2-Cyano-1-(5-methoxycarbonyl-2-thenyl)-aziridine
P = 2-Cyano-1-(2,2-dichloroethyl)-aziridine
Q = 1-(But-2-enyl)-2-cyanoaziridine
R = 2-Cyano-1-(5-methyl-2-nitrobenzyl)-aziridine
S = 1-(2-Chlorobenzyl)-2-cyanoaziridine
T = 2-Cyano-1-(5-methylpyrimidin-4-ylmethyl)-aziridine
U = L-(−)-2-Cyano-(L-(−)-phenylethyl)-aziridine
V = D-(+)-2-Cyano-1-(L-(−)-phenylethyl)-aziridine
W = L-(−)-2-Cyano-1-(D-(+)-phenylethyl)-aziridine
X = 2-Cyano-1-(pyrimidin-2-ylmethyl)-aziridine
Z = 2-Cyano-1-[(2-methoxy-6-methylpyridin-3-yl)-methyl]-aziridine.

2-Cyanoaziridines wherein the nitrogen is substituted by alkyl radicals show only insignificant secondary effects. Thus in opposition to known aziridines the compounds of the invention possess no or only small mutagenic effects proved in the Ames-Test.

Apart from the compounds mentioned in the following examples, preferred compounds according to the present invention for the preparation of pharmaceutical compositions with immune-stimulating action include the following compounds:

2-Cyano-1-(2-dimethylaminoethyl)-aziridine
2-Cyano-1-(2-methylsulphinylethyl)-aziridine
2-Cyano-1-(2-cyanoethyl)-aziridine
1-(3-Chloropropyl)-2-cyanoaziridine
1-(2-Acetamidoethyl)-2-cyanoaziridine
1-(2-Benzamidoethyl)-2-cyanoaziridine
2-Cyano-1-(2-carbamoylethyl)-aziridine
2-Cyano-1-(prop-1-enyl)-aziridine
2-Cyano-1-(but-2-ynyl)-aziridine
2-Cyano-1-(4-hydroxy-3-methoxybenzyl)-aziridine
2-Cyano-1-(cyclohept-2-enylmethyl)-aziridine
2-Cyano-1-(cyclohept-3-enyl)-aziridine
1-(1-Acetylpiperidin-4-yl)-2-cyanoaziridine
2-Cyano-1-(thian-3-yl)-aziridine
2-Cyano-1-(2,2,2-trichloroethyl)-aziridine
2-Cyano-1-(3,4-methylenedioxybenzyl)-aziridine
2-Cyano-1-(2,2,2-trifluoroethyl)-aziridine
2-Cyano-1-(2-nitroethyl)-aziridine
2-Cyano-1-(1-naphthylmethyl)-aziridine
1-Benzyl-aziridin-2-carboxylic acid
1-Allyl-2-cyano-3-phenyl-aziridine 2-Cyano-1-(pent-3-enyl)-aziridine
2-Cyano-1-(4-cyanobenzyl)-aziridine
2-Cyano-1-(2-methylcyclohexyl)-aziridine
2-Cyano-1-(4-methoxycyclohexyl)-aziridine
2-Cyano-1-(pyrimidin-2-yl)-aziridine
2-Cyano-1-(4-phenylbenzyl)-aziridine
2-Cyano-1-(2-methylsulphinyl-benzyl)-aziridine
2-Cyano-1-(2-methylsulphonyl-benzyl)-aziridine
2-Cyano-1-(4-sulphamoylbenzyl)-aziridine
2-Cyano-1-(3-carbamoylbenzyl)-aziridine
1-(4-Acetylbenzyl)-2-cyanoaziridine
1-(2-Acetamido-5-methylbenzyl)-2-cyanoaziridine
2-Cyano-1-(3,4,5-trimethoxybenzyl)-aziridine
2-Cyano-1-(naphth-1-yl)-aziridine
2-Cyano-1-(thiazol-2-yl)-aziridine
Methyl S-2-[(−)-2-cyano-1-aziridine]-propionate
Methyl R-2-[(+)-2-cyano-1-aziridine]-propionate
(+)-1-Allyl-2-cyanoaziridine
(−)-1-Allyl-2-cyanoaziridine
2-Cyano-1-(3-morpholinopropyl)-aziridine
2-Cyano-1-(2-pyrrolidinoethyl)-aziridine
2-Cyano-1-[3-(2-methylpiperidino)-propyl]-aziridine
2-Cyano-1-(2-α-furoylaminoethyl)-aziridine
2-Cyano-1-(4-methylsulphonamidobenzyl)-aziridine
2-Cyano-1-(4-phenoxybenzyl)-aziridine.

The following examples, which are given for the purpose of illustrating the present invention, show some of numerous process variants which can be used for the synthesis of the compounds according to the present invention. The structures of all of the compounds described in the following examples have been confirmed by micro-combustion analyses, NMR spectra and mass spectra:

EXAMPLE 1

1-Allyl-2-cyanoaziridine

A solution of 28.5 g. allylamine and 51 g. triethylamine in 250 ml. toluene is added dropwise, with stirring, at 0° C. to a solution of 66 g. 2-bromoacrylonitrile in 250 ml. toluene. The reaction mixture is subsequently stirred for 3 days at ambient temperature and then filtered with suction. The filtrate is evaporated and the residue is taken up in diethyl ether, extracted once with ice-cold, dilute hydrochloric acid and washed neutral with ice water. This solution is then passed over 400 g. of deactivated aluminum oxide. After evaporation, the residue is distilled twice. There are obtained 28.6 g. (about 53% of theory) 1-allyl-2-cyanoaziridine; b.p.$_{0.2}$: 53°–55° C.

In an analogous manner, by the reaction of 2-bromoacrylonitrile with the appropriate amines, there are obtained the following compounds, which are known from the literature:

(a) 2-cyano-1-methylaziridine (b.p.$_{11}$: 53°–54° C.)
(b) 2-cyano-1-n-propylaziridine (b.p.$_{15}$: 80°–82° C.)
(c) 2-cyano-1-isopropylaziridine (b.p.$_{15}$: 53°–55° C.)
(d) 2-cyano-1-n-pentylaziridine (b.p.$_{0.3}$: 50°–52° C.)
(e) 1,6-bis-(2-cyanoaziridin-1-yl)-hexane (m.p.: 64°–66° C.)
(f) 1-benzyl-2-cyanoaziridine (b.p.$_{0.05}$: 103°–105° C.)
(g) 2-cyano-1-cyclohexylaziridine (b.p.$_{0.1}$: 93°–94° C.)

Compounds (a) to (f) have been described by Gundermann et al. (Chem. Ber., 105, 312/1972) and compound (g) has been described by Wagner-Jauregg (Helv. Chim. Acta, 44, 1237/1961).

In an analogous manner, by the reaction of 2-bromoacrylonitrile with the appropriate amines and subsequent purification by means of a silica gel and/or deactivated aluminum oxide column, there are obtained the following compounds:

(h) 2-Cyano-1-(2-hydroxyethyl)-aziridine
    oily product; yield: 31.1% of theory
(i) Ethyl 3-(2-cyanoaziridin-1-yl)-propionate
    b.p.$_{0.15}$: 105° C.; yield: 33% of theory (dioxane used as solvent)
(k) 2-Cyano-1-(4-hydroxybenzyl)-aziridine
    m.p.: 112°–114° C.; yield: 37% of theory (ethanol used as solvent)
(l) Methyl S-2-[(+)-2-cyano-1-aziridine]-propionate
    m.p. 88°–91° C. recrystallized from diisopropyl ether; $[\alpha]_D^{20} = +99.4°$ c=1 (methanol)
(m) 2-Cyano-1-(cyclohex-1-enylmethyl)-aziridine
    b.p.$_{0.01}$: 103°–105° C.; yield: 42.9% of theory
(n) 2-Cyano-1-(2-thenyl)-aziridine
    b.p.$_{0.1}$: 90°–92° C.; yield: 20% of theory (reaction time 10 days)
(o) 2-Cyano-1-(2-furylmethyl)-aziridine
    b.p.$_{0.1}$: 100°–101° C.; yield: 8.1% of theory (reaction time 10 days)
(p) 2-Cyano-1-(2-methylallyl)-aziridine
    b.p.$_{0.1}$: 36°–38° C.; yield: 16.4% of theory
(q) 1-(1-Adamantyl)-2-cyanoaziridine
    m.p. 62°–64° C.; yield: 51.8% of theory (dioxane used as solvent).

EXAMPLE 2

1-tert.-Butyl-2-cyanoaziridine 6.0 g. 2-Bromo-3-tert-butylaminopropionitrile hydrobromide (prepared by reacting 2,3-dibromopropionitrile with tert.-butylamine; m.p. 188°–190° C.) are dissolved in 50 ml. methanol and heated under reflux for 4 hours with 25 ml. triethanolamine. The solution is then evaporated, neutralized with 2 N sulphuric acid and extracted with diethyl ether and the collected ethereal fractions are dried and evaporated, the residue obtained being subsequently distilled. There is obtained 1.2 g. (about 39.5% of theory) 1-tert.-butyl-2-cyanoaziridine; b.p.$_{0.2}$: 52°–54° C.; m.p. 53°–54° C.

The following compounds are obtained in an analogous manner:

(a) reaction of 2-bromo-3-n-pentylaminopropionitrile hydrochloride (prepared by reacting 2,3-dibromopropionitrile with n-pentylamine; m.p. 133°–135° C.) with triethanolamine gives 2-cyano-n-pentylaziridine; b.p.$_{0.3}$: 50°–52° C.; yield 43% of theory;

(b) reaction of 2-bromo-3-(carbethoxymethylamino)-propionitrile hydrochloride (prepared by reacting 2,3-dibromopropionitrile with glycine ethyl ester; m.p. 70°–75° C.) with triethanolamine gives ethyl 2-cyano-1-aziridineacetate; b.p.$_{0.1}$: 88°–90° C.; yield 34% of theory;

(c) reaction of 2-bromo-3-[(1-carbomethoxyethyl)-amino]-propionitrile (prepared by reacting 2,3-dibromopropionitrile with L-alanine methyl ester; oily substance) with triethylamine gives methyl S-2-[(+)-2-cyano-1-aziridine]-propionate; m.p. 88°–91° C. (recrystallized from diisopropyl ether); $[\alpha]_D^{20} = +99.4°$ (c=1 in methanol).

EXAMPLE 3

1-Allyl-2-cyanoaziridine 4.2 g. Sodium bicarbonate are dissolved in 30 ml. ethanol/15 ml. water, 3.4 g. 2-cyanoaziridine are added thereto and 8.4 g. freshly distilled allyl iodide are added dropwise, whereafter the reaction mixture is stirred for 72 hours at ambient temperature. The solution is then evaporated on a rotary evaporator and the residue is taken up in water and extracted several times with diethyl ether. After drying, the diethyl ether is stripped off and the residue separated with the use of a silica gel column (elution agent: diethyl ether/ligroin 2:1 v/v). The crude 1-allyl-2-cyanoaziridine thus obtained is subsequently distilled. The yield is 1.24 g. (23% of theory) b.p.$_{0.2}$: 53°–55° C.

EXAMPLE 4

2-Cyano-1-phenylaziridine

A mixture of 11.65 g. phenyl azide and 18 g. acrylonitrile is left to stand in the dark for 9 days at ambient temperature. Excess acrylonitrile is then stripped off in a vacuum and the 4-cyano-1-phenyltriazoline-(2) obtained as an intermediate (a sample thereof was crystallized with cyclohexane; m.p. 87°–91° C.) is dissolved in 80 ml. of toluene and heated to 100° C. for 40 minutes, nitrogen thereby being evolved. The toluene is stripped off in a vacuum and the residue distilled. There are obtained 5.9 g. (42% of theory) 2-cyano-1-phenylaziridine; b.p.$_{0.1}$: 109°–111° C.

EXAMPLE 5

3-(2-Cyanoaziridin-1-yl)-acrolein 5.78 g. 2-Cyanoaziridine are added dropwise, with cooling, to 4.6 g. propargyl aldehyde. The reaction mixture is stirred overnight at 20° C., the dark oil obtained is taken up in 500 ml. ethanol and the solution is treated with active charcoal, filtered and concentrated to 50 ml. Upon cooling with ice, the desired product precipitates out and is washed with ethanol/diethyl ether. There are obtained 4.2 g. (41% of theory) 3-(2-cyano-aziridin-1-yl)-acrolein; m.p. 57°–58° C.

The following compounds are obtained in an analogous manner by reacting 2-cyanoaziridine with:
(a) dimethyl acetylene-dicarboxylate: dimethyl 3-(2-cyanoaziridin-1-yl)-fumarate; m.p. 127°–128° C. (recrystallized from ethanol); yield 11% of theory;
(b) ethyl propiolate: ethyl 3-(2-cyanoaziridin-1-yl)-acrylate; oily substance, purified with a silica gel column; yield 24% of theory.

EXAMPLE 6

1-Phenyl-1-(2-cyanoaziridin-1-yl)-2-cyanoethylene 2.7 g. 1-Phenyl-1-(2-carbamoylaziridin-1-yl)-2-cyanoethylene and 5.0 g. triphenyl phosphine are dissolved in a mixture of 400 ml. anhydrous methylene chloride, 1.76 g. triethylamine and 1.2 ml. anhydrous carbon tetrachloride and the reaction mixture then stirred under reflux, the dehydration reaction being monitored by thin layer chromatography. The reaction mixture is then evaporated and the residue purified on a silica gel column with the elution mixture chloroform/acetone/cyclohexane (5:5:1 v/v/v). The desired fraction is caused to crystallize with ligroin. There is obtained 0.7 g. (23.5% of theory) 1-phenyl-1-(2-cyanoaziridin-1-yl)-2-cyanoethylene; m.p. 95° C. (recrystallized from diethyl ether).

The following compounds are obtained in an analogous manner from the indicated starting materials:
(a) 1-(2-Carbamoylaziridin-1-yl)-2-carbethoxy-cyclohex-1-ene
1-(2-Cyanoaziridin-1-yl)-2-carbethoxy-cyclohex-1-ene; m.p.: 101°–104° C.; yield: 54.5% of theory
(b) L-(−)-1-(L-(−)-Phenylethyl)-aziridine-2-carboxamide (see Example 14)
L-(−)-2-Cyano-(L-(−)-phenylethyl)-aziridine; m.p.: 44°–48° C.; yield: 45% of theory $[\alpha]_D^{20}$: −129.4° (c=1 in methanol)
(c) D-(+)-1-(L-(−)-Phenylethyl)-aziridine-2-carboxamide (see Example 14a)
D-(+)-2-Cyano 1-(L-(−)-phenylethyl)-aziridine; oily substance; yield: 51% of theory $[\alpha]_D^{20}$: +58.8° (c=1 in methanol)
(d) L-(−)-1-(D-(+)-Phenylethyl)-aziridine-2-carboxamide (see Example 14b)
(L-(−)-2-Cyano-1-(D-(+)-phenylethyl)-aziridine; oily substance; yield: 74% of theory $[\alpha]_D^{20}$: −53.5° (c=1 in methanol)
(e) D-(+)-1-(D-(+)-Phenylethyl)-aziridine-2-carboxamide (see Example 14c)
D-(+)-2-Cyano-1-(D-(+)-phenylethyl)-aziridine; m.p. 45°–48° C.; yield: 62% of theory $[\alpha]_D^{20}$: +128.1° (c=1 in methanol)

EXAMPLE 7

1-(2-Carbamoylaziridin-1-yl)-1-(p-methoxycarbonylphenyl)-ethylene 2.7 g. p-Methoxycarbonylacetophenone and 1.03 g. 2-cyanoaziridine are mixed and, after the addition of 1.05 ml. triethylamine, stirred for 3 hours at 60° C. After cooling, the reaction mixture is stirred with diethyl ether. The residue is brought to crystallization with a mixture of chloroform and methanol (9:1 v/v). There is obtained 0.9 g. (24% of theory) 1-(2-carbamoylaziridin-1-yl)-1-(p-methoxycarbonylphenyl)-ethylene; m.p. 140°–141° C. (decomp.).

The following compounds are obtained in an analogous manner by reacting 2-cyanoaziridine with
(a) acetophenone:
1-phenyl-1-(2-carbamoylaziridin-1-yl)-ethylene; m.p. 93°–96° C.; yield 16% of theory
(b) ω-cyanoacetophenone:
(1-phenyl-1-(2-carbamoylaziridin-1-yl)-2-cyanoethylene; m.p. 164°–167° C. (recrystallized from ethyl acetate); yield 84.5% of theory
(c) ethyl cyclohexanone-2-carboxylate:
1-(2-carbamoylaziridin-1-yl)-2-carboethoxycyclohex-1-ene; m.p. 168°–170° C.; yield 17% of theory (reaction time 70 hours; crystallized by trituration with ethyl acetate)
(d) 1-methylpiperidinone-(4):
4-(2-carbamoylaziridin-1-yl)-1-methyl-3,4-dehydropiperidine; m.p. 149°–150° C.; yield 12% of theory (reaction time 24 hours, crystallized by trituration with isopropanol).

EXAMPLE 8

1-Allyl-2-cyano-3-methylaziridine 13.4 g. Crotonitrile are mixed at ambient temperature, within the course of 2 hours, with 32 g. bromine and the solution then heated to 30° C. until decolorized. The reaction mixture is diluted with 100 ml. diethyl ether and cooled to 0° C. A solution of 20.2 g. triethylamine in 50 ml. diethyl ether is added dropwise thereto and the reaction mixture further stirred for 1 hour at 0° C. To the suspension obtained is added at 0° C. a mixture of 20.2 g. triethylamine and 11.4 g. allylamine in 100 ml. diethyl ether and the reaction mixture stirred for 4 days at ambient temperature. The precipitate obtained is filtered off with suction, washed with diethyl ether and the ethereal solution, after drying, passed over 250 g. deactivated aluminum oxide. The eluate is subsequently evaporated and fractionated. There are obtained 10.3 g. (42.2% of theory) 1-allyl-2-cyano-3-methylaziridine; b.p.$_{0.1}$: 55°–57° C.

EXAMPLE 9

Ethyl 1-benzylaziridine-2-carboxylate 55.3 ml. Triethylamine are added, with stirring, at 0° C. to 52 g. ethyl 2,3-dibromopropionate in 250 ml. toluene and, after 2 hours, a solution of 21.4 g. benzylamine in 250 ml. toluene added thereto. The reaction mixture is subsequently further stirred for 3 days at ambient temperature. The suspension is then shaken out several times with water and the organic phase is dried and evaporated and the residue is taken up in diethyl ether. The ethereal solution is passed over 400 g. deactivated aluminum oxide and the eluate is evaporated and fractionated. There are obtained 30.7 g. (about 75% of theory) ethyl 1-benzylaziridine-2-carboxylate; b.p.$_{0.03}$: 98°–101° C.

The following compounds are obtained in an analogous manner by reacting ethyl 2,3-dibromopropionate with:
(a) methylamine:
  ethyl 1-methylaziridine-2-carboxylate; b.p.$_{18}$: 70°–72° C.; yield 40% of theory
(b) allylamine:
  ethyl 1-allylaziridine-2-carboxylate; b.p.$_{12}$: 91°–92° C.; yield 24% of theory.

EXAMPLE 10

2-Cyano-1-methylaziridine 5.0 g. 1-(2-Cyanoethyl)-1-methyl-2,2,2-trimethylhydrazinium iodide (m.p. 125°–130° C.) are heated to 40° C. for 12 hours in a solution of 0.2 g. sodium methylate in 30 ml. methanol, trimethylamine being liberated during the reaction. Subsequently, the reaction mixture is evaporated, the residue is passed over a silica gel column (elution agent: acetone/toluene 1:1 v/v) and the crude product so obtained is distilled twice. There is obtained 0.35 g. (about 23% theory) 2-cyano-1-methylaziridine; b.p.$_{11}$: 53°–54° C.

EXAMPLE 11

In a manner analogous to that described in Example 1, the following compounds are obtained by reacting 2-bromoacrylonitrile with:
(a) 2-methylthiobenzylamine:
  2-cyano-1-(2-methylthiobenzyl)-aziridine; oily product; yield 54% of theory
(b) 3,4-dimethoxybenzylamine:
  2-cyano-1-(3,4-dimethoxybenzyl)-aziridine; oily product; yield 25% of theory
(c) 4-methylbenzylamine:
  2-cyano-1-(4-methylbenzyl)-aziridine; b.p.$_{0.05}$: 113°–115° C.; yield 23% of theory
(d) cyclopropylamine:
  2-cyano-1-cyclopropylaziridine; b.p.$_{1.5}$: 70° C.; yield 22% of theory
(e) 2-methyl-3-carbethoxybenzylamine:
  2-cyano-1-(2-methyl-3-carbethoxybenzyl)-aziridine; b.p.$_{0.01}$: 168°–170° C.; m.p. 40°–43° C.; yield 20% of theory
(f) 2-chloroethylamine hydrochloride:
  1-(2-chloroethyl)-2-cyanoaziridine (using dioxane as solvent); b.p.$_{0.1}$: 74° C.; yield 5.1% of theory
(g) 4-aminotetrahydropyran:
  1-(4-tetrahydropyranyl)-2-cyanoaziridine (using dioxane as solvent); m.p. 74°–76° C.; yield 13.2% of theory
(h) 2-methoxyethylamine:
  2-cyano-1-(2-methoxyethyl)-aziridine; b.p.$_{0.2}$: 80° C.; yield 17.5% of theory
(i) 2-phenoxyethylamine:
  2-cyano-1-(2-phenoxyethyl)-aziridine; b.p.$_{0.05}$: 115° C.; yield 38.8% of theory.

EXAMPLE 12

1-Benzylaziridine-2-carboxamide 0.7 g. Ethyl 1-benzylaziridine-2-carboxylate is stirred for 16 hours at ambient temperature with 10 ml. concentrated aqueous ammonia solution. The precipitated crystals are filtered off with suction and washed with a little water. There is obtained 0.45 g. (about 75% of theory) 1-benzylaziridine-2-carboxamide; m.p. 114°–116° C.

EXAMPLE 13

Analogously to Example 1, by the reaction of 2-bromoacrylonitrile with the indicated starting materials, there are obtained the following compounds:
(a) 5-Methoxycarbonyl-2-thenylamine:
  2-Cyano-1-(5-methoxycarbonyl-2-thenyl)-aziridine; m.p.: 51°–54° C.; yield: 49% of theory
(b) 5-Methoxycarbonyl-2-furfurylamine:
  2-Cyano-1-(5-methoxycarbonyl-2-furfuryl)-aziridine; m.p.: 86°–89° C; yield: 46% of theory
(c) 2,2-Dichloroethylamine:
  2-Cyano-1-(2,2-dichloroethyl)-aziridine; m.p.: 94°–95° C.; yield: 16% of theory
(d) But-2-enylamine:
  1-(But-2-enyl)-2-cyanoaziridine; b.p.$_{0.1}$: 60°–61° C.; yield: 70% of theory
(e) 5-Methylpyrimidin-4-ylmethylamine:
  2-Cyano-1-(5-methylpyrimidin-4-ylmethyl)-aziridine; m.p.: 88°–92° C. (recrystallized from isopropanol); yield: 56% of theory
(f) 2-Hydroxy-6-methylpyrimidin-3-ylmethylamine:
  2-Cyano-1-[(2-hydroxy-6-methylpyrimidin-3-yl)-methyl]-aziridine; m.p.: 187°–190° C. (recrystallized from water); yield: 47% of theory
(g) Aminoacetaldehyde dimethyl acetal:
  2-Cyano-1-(2,2-dimethoxy-1-ethyl)-aziridine; b.p.$_{0.1}$: 90°–92° C.; yield: 70% of theory
(h) 1,6-Dimethyl-2-oxo-pyridin-3-ylmethylamine:
  2-Cyano-1-[(1,6-dimethyl-2-oxo-pyridin-3-yl)-methyl]-aziridine; m.p.: 82°–84° C.; yield: 78% of theory
(i) 2-Methoxy-6-methylpyridin-3-ylmethylamine:
  2-Cyano-1-[(2-methoxy-6-methylpyridin-3-yl)-methyl]-aziridine; m.p.: 70°–73° C. (recrystallized from isopropanol); yield: 69% of theory
(k) 2,5-Dimethyl-pyrimidin-4-ylmethylamine:
  2-Cyano-1-[(2,5-dimethyl-pyrimidin-4-yl)-methyl]-aziridine; m.p.: 88°–92° C. (recrystallized from isopropanol); yield: 82% of theory
(l) 4-Methylthiazol-2-ylmethylamine:
  2-Cyano-1-(4-methylthiazol-2-ylmethyl)-aziridine; m.p.: 73°–75° C.; yield: 21% of theory
(m) Prop-2-ynylamine:

2-Cyano-1-(prop-2-ynyl)-aziridine; b.p.$_{0.1}$: 48° C.; yield: 28% of theory (n) Tetrahydrofurfurylamine:
  2-Cyano-1-tetrahydrofurfuryl-aziridine; b.p.$_{0.1}$: 95° C.; yield: 20% of theory (o) 3-Trifluoromethyl-benzylamine:
  2-Cyano-1-(3-trifluoromethylbenzyl)-aziridine; b.p.$_{0.15}$: 92° C.; yield: 31% of theory (p) 3-Methylthiopropylamine:
  2-Cyano-1-(3-methylthiopropyl)-aziridine; b.p.$_{0.05}$: 110° C.; yield: 18% of theory (q) 2-Methylsulphonylethylamine:
  2-Cyano-1-(2-methylsulphonylethyl)-aziridine; oily substance; yield: 47% of theory (r) Phenethylamine:
  2-Cyano-1-phenethyl-aziridine; b.p.$_{0.05}$: 122°-124° C.; yield: 18% of theory (s) Cinnamylamine:
  1-Cinnamyl-2-Cyanoaziridine; b.p.$_{0.05}$: 138°-140° C.; yield: 13% of theory (t) But-3-ynylamine:
  1-(But-3-ynyl)-2-cyanoaziridine; b.p.$_{0.1}$: 70°-71° C.; yield: 68% of theory (u) 2-Norbornylamine:
  2-Cyano-1-(2-norbornyl)-aziridine; b.p.$_{0.05}$: 84°-85° C.; yield: 20% of theory (v) 2-Chlorobenzylamine;
  1-(2-Chlorobenzyl)-2-cyanoaziridine; m.p.: 55°-57° C. (recrystallized from isopropanol); yield: 36% of theory (w) Pyrimidin-2-ylmethylamine:
  2-Cyano-1-(pyrimidin-2-ylmethyl)-aziridine; m.p.: 72°-76° C. (recrystallized from isopropanol); yield: 33% of theory (x) 5-Methyl-2-nitrobenzylamine:
  2-Cyano-1-(5-methyl-2-nitrobenzyl)-aziridine; m.p.: 95°-96° C. (recrystallized from isopropanol); yield: 41% of theory (y) R-(−)-Alanine methyl ester:
  Methyl-R-(−)-2-[L-(−)-2-Cyano-1-aziridin]-propionate; m.p.: 90°-91° C. (recrystallized from isopropyl ether); yield: 12% of theory; $[\alpha]_D^{20}$: −99.1° (c=1 in methanol).

EXAMPLE 14

L-(−)-1-(L-(−)-Phenylethyl)-aziridine-2-carboxamide 5.6 g. Ethyl L-(−)-1-(L-(−)-phenylethyl)-aziridine-2-carboxylate (see Example 15) are dissolved in 55 ml. concentrated aqueous ammonia solution and 55 ml. ethanol and left to stand for 72 hours at ambient temperature. The solution is then evaporated and residue triturated with diethyl ether. The white precipitate is filtered off with suction and then washed with diethyl ether. There are obtained 3.7 g. (about 79% of theory) L-(−)-1-(L-(−)-phenylethyl)-aziridine-2-carboxamide; m.p. 108°-111° C.; $[\alpha]_D^{20}$: −116.5° (c=1 in methanol).

The following compounds are obtained in an analogous manner from:

(a) ethyl D-(+)-1-(L-(−)-phenylethyl)-aziridine-2-carboxylate (see Example 15):
  D-(+)-1-(L-(−)-phenylethyl)-aziridine-2-carboxamide; m.p. 95°-98° C.; yield 70% of theory; $[\alpha]_D^{20}$: +40.5° (c=1 in methanol)

(b) ethyl L-(−)-1-(D-(+)-phenylethyl)-aziridine-2-carboxylate (see Example 15a):

L-(−)-1-(D-(+)-phenylethyl)-aziridine-2-carboxamide; m.p. 94°-97° C.; yield 76% of theory; $[\alpha]_D^{20}$: −38.8° (c=1 in methanol)

(c) ethyl D-(+)-1-(D-(+)-phenylethyl)-aziridine-2-carboxylate (see Example 15b):
  D-(+)-1-(D-(+)-phenylethyl)-aziridine-2-carboxamide; m.p. 102°-104° C.; yield: 77% of theory; $[\alpha]_D^{20}$: +115° (c=1 in methanol).

EXAMPLE 15

Ethyl L-(−)-1-(L-(−)-phenylethyl)-aziridine-2-carboxylate and ethyl D-(+)-1-(L-(−)-phenylethyl)-aziridine-2-carboxylate 15 g. Triethanolamine in 20 ml. ethanol are added, with stirring, to 26 g. ethyl 2,3-dibromopropionate in 60 ml. ethanol and, after 1 hour, there are simultaneously added a solution of 12.1 g L-(−)-phenylethylamine in 20 ml. ethanol and a solution of 15 g. triethanolamine in 20 ml. ethanol. The suspension is stirred for 12 hours at ambient temperature and filtered off with suction. The filtrate is evaporated and the residue separated over a silica gel column into the diastereomers using, as elution agent, diethyl ether/ligroin 2:1 v/v).

Yield of L,L-isomer: 39% of theory;
oily substance; $[\alpha]_D^{20}$: −90° (c=1 in ethanol)
yield of D.L-isomer: 47% of theory
oily substance; $[\alpha]_D^{20}$: +53.2° (c=1 in ethanol)

In an analogous manner, by the reaction of ethyl 2,3-dibromopropionate with D-(+)-phenylethylamine, there are obtained the following compounds:

(a) ethyl L-(−)-1-(D-(+)-phenylethyl)-aziridine-2-carboxylate; oily substance; yield 39% of theory; $[\alpha]_D^{20}$: −57.9° (c=1 in ethanol); and (b) ethyl D-(+)-1-(D-(+)-phenylethyl)-aziridine-2-carboxylate; oily substance; yield 39% of theory; $[\alpha]_D^{20}$: +89.7° (c=1 in ethanol).

EXAMPLE 16

2-Cyano-1-(5-carboxy-2-thenyl)-aziridine 95 ml. 0.1 N Aqueous sodium hydroxide solution are added dropwise, with stirring, to 2.1 g. 2-cyano-1-(5-methoxycarbonyl-2-thenyl)-aziridine (see Example 13a) in 21 ml. acetone. When no more ester can be detected by thin layer chromatography, the reaction mixture is evaporated in a vacuum, acidified with dilute hydrochloric acid and extracted with ethyl acetate. The evaporation residue is crystallized with diethyl ether. There is obtained 1.2 g (61% of theory) 2-cyano-1-(5-carboxy-2-thenyl)-aziridine; m.p. 108°-111° C. The sodium salt melts with decomposition at 238°-243° C.

(a) In an analogous manner, from 2-cyano-1-(5-methoxy-carbonyl-2-furfuryl)-aziridine (see Example 13b), there is obtained 2-cyano-1-(5-carboxy-2-furfuryl)-aziridine; m.p. 108°-111° C.; yield 44% of theory.

EXAMPLE 17

1-Benzyl-2-cyanoaziridine 2.74 g. 3-Benzyl-4-cyano-2-oxazolidinone (m.p. 81°-83° C.; prepared by reacting 4-cyano-2-oxazolidinone (m.p. 95°-96° C.) with benzyl bromide in the presence of sodium hydride) are heated under reflux for 3 hours in 20 ml. o-dichlorobenzene, with the addition of 1.5 g. triethanolamine. After cooling, the reaction mixture is extracted with ice-cold 1 N hydrochloric acid, washed neutral with water, dried and the organic phase fractionated. There are obtained 0.47 g. (about 31% of theory) 1-benzyl-2-cyanoaziridine; b.p.$_{0.05}$: 103°–105° C.

EXAMPLE 18

The following examples are concerned with pharmaceutical compositions which contain compounds of general formula (I) or salts thereof.

EXAMPLE A (tablets)

| active material | X mg. X = up to 40.0 mg. |
|---|---|
| lactose | ad 60.0 mg. |
| polyvinylpyrrolidone | 2.0 mg. |
| microcrystalline cellulose | 8.0 mg. |
| sodium carboxymethyl-amylopectin | 4.0 mg. |
| silicic acid, highly dispersed | 0.5 mg. |
| talc | 5.0 mg. |
| magnesium stearate | 0.5 mg. |
| end weight | 80.0 mg. |

For liquid active materials in dosages of up to about 40 mg.:

| active material | X mg. X = up to 40.0 mg. |
|---|---|
| silicic acid, highly dispersed | ad 100.00 mg. |
| lactose | 135.0 mg. |
| polyvinylpyrrolidone | 10.0 mg. |
| microcrystalline cellulose | 25.0 mg. |
| sodium carboxymethyl-amylopectin | 10.0 mg. |
| silicic acid, highly dispersed | 2.0 mg. |
| talc | 15.0 mg. |
| magnesium stearate | 3.0 mg. |
| end weight | 300.0 mg. |

The active materials and adjuvants are mixed, optionally granulated and pressed into dragee cores using conventional machines. The dragee cores are then coated in the usual manner with a film which is resistant to gastric juices but is soluble in intestinal juice (for example an anionic polymer of methacrylic acid and methyl methacrylate).

| active material | X mg. X = up to 40.0 mg. |
|---|---|
| lactose | ad 60.0 mg. |
| magnesium oxide | 100.0 mg. |
| polyvinylpyrrolidone | 2.0 mg. |
| microcrystalline cellulose | 8.0 mg. |
| sodium carboxymethyl-amylopectin | 4.0 mg. |
| silicic acid, highly dispersed | 0.5 mg. |
| talc | 5.0 mg. |
| magnesium stearate | 0.5 mg. |
| end weight | 180.0 mg. |

The active material and adjuvants are mixed, optionally granulated and pressed into tablets.

EXAMPLE B (injection solution)

As preparations suitable for injection, which contain 1-allyl-2-cyanoaziridine, there can be mentioned aqueous solutions of polyethylene glycol 400, ethylene glycol monoethyl ether and ethanol, as well as a solution of the active material in "Miglyol" 812 neutral oil, the latter adjuvant only being used for intramuscular administration. The compositions are formulated in such a manner that the pH value, buffer capacity and titration basicity do not deviate very much from the physiological values. These injection compositions withstand sterilization in an autoclave for 20 minutes at 121° C. without any chemical change taking place.

EXAMPLE

| | | | | |
|---|---|---|---|---|
| 1-allyl-2-cyanoaziridine | 40 mg. | 40 mg. | 40 mg. | 40 mg. |
| polyethylene glycol 400 | 1 mg. | | | |
| water | 3 mg. | 3 mg. | 4 mg. | |
| ethylene glycol monoethyl ether | | 2 mg. | 1 mg. | |
| "Miglyol" 812 neutral oil | | | | 3 mg. |
| ethanol | 1 mg. | | | |

The solvents are mixed together with the active material in a kettle. The solution thus obtained is sterilized by filtration through filter layers of Fibrafix AF. The first 15 liters are pre-runnings which are recycled to the batch. The membrane filtration is carried out directly on a filling machine via a Sartorius membrane filter of 0.2 μm. pore size. The solution is subsequently filled in 5 ml. ampoules and then sterilized in an autoclave for 20 minutes at 121° C.

EXAMPLE C (soft gelatine capsules)

The active material is soluble in organic compounds, such as "Miglyol" 812 (triglyceride of saturated fatty acids with a chain length of C=30), mixtures of ethanol in water, polyethylene glycol 400 in water and ethylene glycol monoethyl ether in water and can, in such solutions, be worked up to give soft gelatine capsules. The active material can also be worked up in admixture with wax, soya bean oil, lecithin and hydrogenated fats to give a conventional soft gelatine formulation.

EXAMPLE

| | | | | | |
|---|---|---|---|---|---|
| 1-Allyl-2-cyano-aziridine | 40 mg. | 40 mg. | 40 mg. | 40 mg. | 40 mg. |
| bees' wax | 20 mg. | | | | |
| hydrogenated soya bean oil | 140 mg. | | | | |
| soya lecithin | 70 mg. | | | | |
| polyethylene glycol 400 | | 210 mg. | | | 180 mg. |
| "Miglyol" 812 | | 100 mg. | 100 mg. | 200 mg. | 35 mg. |
| ethylene glycol monoethyl ether | | | 210 mg. | 50 mg. | |
| ethyl acetate | | | | 43 mg. | 85 mg. |

The active material can be mixed with the appropriate amounts of the above-mentioned adjuvants and worked up on a special machine to give soft gelatine capsules of various sizes and dosages.

EXAMPLE D (drops and syrups)

| | ml. | ml. | ml. | ml. | ml. | ml. |
|---|---|---|---|---|---|---|
| (a) 1-allyl-2-cyano aziridine | 2.5 | 2.5 | 2.5 | 2.5 | 2.5 | 2.5 |
| polyethylene glycol 400 | — | 9.5 | 10.5 | 7.5 | — | 7.5 |
| ethyl acetate | — | 8.0 | 5.0 | — | 2.5 | — |

| | | | | |
|---|---|---|---|---|
| ethylene glycol monomethyl ether | 12.0 | — | — | 9.0 | 3.0 | 3.0 |
| "Miglyol" 812 | 5.5 | — | 2.0 | 1.0 | 12.0 | |
| water | | | | | | 7.0 |

| | ml. | ml. | ml. | ml. |
|---|---|---|---|---|
| (b) 1-Allyl-2-cyano-aziridine | 2.5 | 2.5 | 2.5 | 2.5 |
| polyethylene glycol 400 | — | — | 12.0 | — |
| ethylene glycol monoethyl ether | 2.0 | — | — | 52.0 |
| ethyl acetate | — | — | — | 43.0 |
| "Miglyol" 812 | — | 154.0 | — | 80.0 |
| water | 134.0 | | 143.0 | |

The active material is mixed with appropriate amounts of the above-mentioned adjuvants. The mixture is sterilized by means of filter layers of Fibrafix AF and also filtered through membrane filters with a pore size of 0.2 μm., followed by filling into 20 ml. drop bottles or into 200 ml. syrup bottles.

The present invention also provides pharmaceutical compositions comprising the new compound and/or at least one solid or liquid pharmaceutical diluent or carrier.

For the preparation of pharmaceutical compositions, an N-substituted aziridine-2-carboxylic acid derivative the invention is mixed in known manner with an appropriate pharmaceutical carrier substance and formed, for example, into tablets or dragees or, with the addition of appropriate adjuvants, suspended or dissolved in water or an oil, for example olive oil, and placed in capsules. Since the active material is acid labile, the composition is provided with a coating which only dissolves in the alkaline medium of the intestines or an appropriate carrier material, for example a high molecular weight fatty acid or carboxymethyl-cellulose is mixed therewith. Examples of solid carrier materials include starch, lactose, mannitol, methyl cellulose, talc, highly dispersed silicic acids, high molecular weight fatty acids (for example stearic acid), gelatin, agar-agar, calcium phosphate, magnesium stearate, animal and vegetable fats and solid high molecular weight polymers (such as polyethylene glycols). Compositions suitable for oral administration can, if desired, contain flavoring and/or sweetening materials.

However, the active material is preferably injected. As injection medium, it is preferred to use water which contains the additives usual in the case of injection solutions, such as stabilizing agents, solubilizing agents and/or weakly alkaline buffers. Additives of this type include, for example, phosphate and carbonate buffers, ethanol, complex-forming agents (for example ethylenediamine-tetraacetic acid and the non-toxic salts thereof) and high molecular weight polymers (for example liquid polyethylene oxide) for viscosity regulation.

For treatment of humans the active material may be applied one or more times with each dose containing about 25 to 3000 and preferably 50 to 500 mg of active material.

It will be appreciated that the instant specification and examples are set forth by way of illustration and not limitation, and that various modifications and changes may be made without departing from the spirit and scope of the present invention.

What we claim is:

1. A 2-cyanoaziridine derivative of the formula

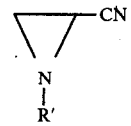

wherein
R' is a methyl, ethyl or n-propyl residue, substituted by a thienyl radical, the thienyl radical being optionally substituted by one carboxyl, methoxycarbonyl, ethoxycarbonyl or n-propoxycarbonyl,
or a pharmacologically acceptable salt thereof.

2. A compound according to claim 1, wherein such compound is 2-cyano-1-(5-methoxycarbonyl-2-thenyl)-aziridine of the formula

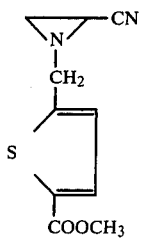

or a pharmacologically acceptable acid addition salt thereof.

3. An immuno-stimulating composition comprising an immuno-stimulating effective amount of an aziridine-2-carboxylic acid derivative or salt thereof as defined in claim 1 and a pharmacologically acceptable diluent.

4. A method of stimulating an immune response in a patient which comprises administering to the patient an immunostimulating effective amount of an aziridine-2-carboxylic acid derivative or salt thereof according to claim 1.

* * * * *